(12) United States Patent
Beuckelaere et al.

(10) Patent No.: US 11,765,794 B2
(45) Date of Patent: Sep. 19, 2023

(54) PORTABLE HEATING APPARATUS WITH TEMPERATURE-RETAINING COMPONENT

(71) Applicant: FKA Distributing Co., LLC, Commerce Township, MI (US)

(72) Inventors: Amanda Beuckelaere, Royal Oak, MI (US); Chaunta Johns, West Bloomfield, MI (US); Mark Straight, Novi, MI (US); Ray Morency, Waterford, MI (US)

(73) Assignee: FKA Distributing Co., LLC, Commerce Township, MI (US)

( * ) Notice: Subject to any disclaimer, the term of this patent is extended or adjusted under 35 U.S.C. 154(b) by 818 days.

(21) Appl. No.: 16/804,992

(22) Filed: Feb. 28, 2020

(65) Prior Publication Data

US 2020/0281046 A1 Sep. 3, 2020

Related U.S. Application Data

(60) Provisional application No. 62/811,892, filed on Feb. 28, 2019.

(51) Int. Cl.
*H05B 3/36* (2006.01)
*A61F 7/00* (2006.01)
*H05B 3/34* (2006.01)

(52) U.S. Cl.
CPC ............... *H05B 3/36* (2013.01); *A61F 7/007* (2013.01); *H05B 3/342* (2013.01); *H05B 2203/003* (2013.01)

(58) Field of Classification Search
CPC ...... A61F 2007/0004; A61F 2007/0025; A61F 2007/003; A61F 2007/0071;
(Continued)

(56) References Cited

U.S. PATENT DOCUMENTS

| | | |
|---|---|---|
| 5,451,747 A | 9/1995 | Sullivan et al. |
| 5,835,983 A | 11/1998 | McMahen et al. |

(Continued)

FOREIGN PATENT DOCUMENTS

| | | |
|---|---|---|
| AU | 740320 B2 | 6/1999 |
| CN | 2655850 Y | 11/2004 |

(Continued)

OTHER PUBLICATIONS

Extended European Search Report for Application No. 20763914.7-1113, dated Nov. 11, 2022, 10 pages.

(Continued)

*Primary Examiner* — Dana Ross
*Assistant Examiner* — James F Sims, III
(74) *Attorney, Agent, or Firm* — Brooks Kushman P.C.

(57) ABSTRACT

A portable heating apparatus includes a top layer and a bottom layer connected to the top layer to form a cavity. An electric heating element is disposed within the cavity, and a temperature-retaining component, such as a gel layer, is affixed within the cavity adjacent to the electric heating element and adjacent to the top layer. A power cord is in electrical communication with the electric heating element and connectable to a power source to provide power to the electric heating element, the power cord detachable from the portable heating apparatus. The temperature-retaining component is capable of retaining heat generated by the electric heating element and creating a generally uniform distribution of heat across the top layer.

15 Claims, 11 Drawing Sheets

(58) Field of Classification Search
CPC ...... A61F 2007/0074; A61F 2007/0093; A61F 2007/0094; A61F 2007/0219; A61F 2007/0228; A61F 2007/0231; A61F 2007/0244; A61F 2007/108; A61F 7/007; A61F 7/02; A61F 7/10; H05B 2203/003; H05B 2203/014; H05B 2203/02; H05B 3/342; H05B 3/345; H05B 3/36
USPC .................................................. 219/528–531
See application file for complete search history.

(56) References Cited

U.S. PATENT DOCUMENTS

| | | | |
|---|---|---|---|
| 6,289,889 | B1 | 9/2001 | Bell et al. |
| 6,409,748 | B1 | 6/2002 | DeCarlo et al. |
| 6,416,534 | B1 | 7/2002 | Montagnino et al. |
| 8,143,559 | B2 | 3/2012 | Chow |
| 8,164,035 | B2 | 4/2012 | Chang |
| 8,173,938 | B2 | 5/2012 | Robst |
| 8,383,992 | B2 | 2/2013 | Wang et al. |
| 9,290,890 | B2 * | 3/2016 | Naylor .................... E01C 23/03 |
| 9,320,084 | B2 | 4/2016 | Weiss et al. |
| 9,360,518 | B2 | 6/2016 | Kohn et al. |
| 2009/0114633 | A1 * | 5/2009 | Naylor .................... H05B 3/36 219/528 |
| 2011/0286138 | A1 | 11/2011 | Shi et al. |
| 2012/0140362 | A1 * | 6/2012 | Robins .................... H05B 3/36 361/18 |
| 2015/0021313 | A1 | 1/2015 | Chang |
| 2017/0065453 | A1 | 3/2017 | Carey et al. |
| 2018/0216290 | A1 * | 8/2018 | Feng .................... D06C 23/04 |

FOREIGN PATENT DOCUMENTS

| | | | |
|---|---|---|---|
| CN | 201097239 | Y | 8/2008 |
| CN | 100563900 | C | 12/2009 |
| CN | 201464940 | U | 5/2010 |
| CN | 201845243 | U | 5/2011 |
| CN | 101592962 | B | 12/2011 |
| CN | 101847022 | B | 5/2012 |
| CN | 203352824 | U † | 12/2013 |
| CN | 203480335 | U | 3/2014 |
| CN | 203884009 | U | 10/2014 |
| CN | 102781379 | B | 3/2015 |
| CN | 103294083 | B | 5/2015 |
| CN | 204499545 | U | 7/2015 |
| CN | 103439994 | B | 4/2017 |
| CN | 107124775 | A | 9/2017 |
| CN | 206728310 | U | 12/2017 |
| CN | 107978121 | A | 5/2018 |
| CN | 208188700 | U | 12/2018 |
| EP | 1645167 | B2 | 7/2010 |
| KR | 1020120050261 | A | 5/2012 |
| KR | 1020140101623 | A | 8/2014 |

OTHER PUBLICATIONS

International Preliminary Report on Patentability for PCT Application No. PCT/IB2020/000157, dated Sep. 10, 2021, 8 pages.
International Search Report and Written Opinion for Application No. PCT/IB2020/000157, dated Jul. 24, 2020, 11 pages.

* cited by examiner
† cited by third party

PORTABLE HEATING APPARATUS WITH TEMPERATURE-RETAINING COMPONENT

CROSS-REFERENCE TO RELATED APPLICATIONS

This application claims the benefit of U.S. provisional application Ser. No. 62/811,892 filed Feb. 28, 2019, the disclosure of which is hereby incorporated in its entirety by reference herein.

TECHNICAL FIELD

Embodiments relate to a portable heating apparatus, such as a heating pad or wrap, with a temperature-retaining component, such as a gel layer.

BACKGROUND

Heating pads or wraps are designed for supplying heat to various parts of the body, such as the back, arms and legs. Electric heating pads have a constant source of power for maintaining a maximum heat level, but their use is restricted to locations within reach of a power outlet. While many heating pads offer comfort and convenience to a user, often heating pads are not constructed to provide efficient and effective heat treatment of the body while also providing portability. A continuing need exists for heating pads and wraps which can meet user requirements for heat therapy while still being easy and cost-effective to manufacture.

SUMMARY

In one or more embodiments, a portable heating apparatus includes a top layer and a bottom layer connected to the top layer to form a cavity. An electric heating element is disposed within the cavity, and a temperature-retaining component, such as a gel layer, is affixed within the cavity adjacent to the electric heating element and adjacent to the top layer. A power cord is in electrical communication with the electric heating element and connectable to a power source to provide power to the electric heating element, the power cord detachable from the portable heating apparatus. The temperature-retaining component is capable of retaining heat generated by the electric heating element and creating a generally uniform distribution of heat across the top layer.

In one or more embodiments, a portable heating apparatus includes a top layer and a bottom layer connected to the top layer to form a cavity. An electric heating element is disposed within the cavity, a padding material is disposed within the cavity between the electric heating element and the bottom layer, and a gel layer is affixed within the cavity between the electric heating element and the top layer. A power cord is in electrical communication with the electric heating element and connectable to a power source to provide power to the electric heating element, the power cord detachable from the portable heating apparatus. The gel layer is capable of retaining heat generated by the electric heating element and creating a generally uniform distribution of heat across the top layer.

In one or more embodiments, a portable heating apparatus includes a main body including an outer, top layer and an inner, bottom layer connected to the top layer, the top and bottom layers forming a cavity therebetween, with a first strap and a second strap extending from the main body. An electric heating element is disposed within the cavity, and a temperature-retaining component is affixed within the cavity adjacent to the electric heating element and adjacent to the bottom layer. A power cord is in electrical communication with the electric heating element and connectable to a power source to provide power to the electric heating element, the power cord detachable from the portable heating apparatus. The temperature-retaining component is capable of retaining heat generated by the electric heating element and creating a generally uniform distribution of heat across the bottom layer.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

With reference first to FIGS. 1-6, a heating pad 10 with a temperature-retaining component is illustrated. In one or more embodiments, the heating pad 10 may be substantially rectangular and have dimensions, for example, of approximately 12 inches by 15 inches (FIG. 1), or approximately 12 inches by 24 inches (FIG. 2), or any other suitable size. Of course, other shapes and sizes are also fully contemplated, as described further below.

Figure 1:
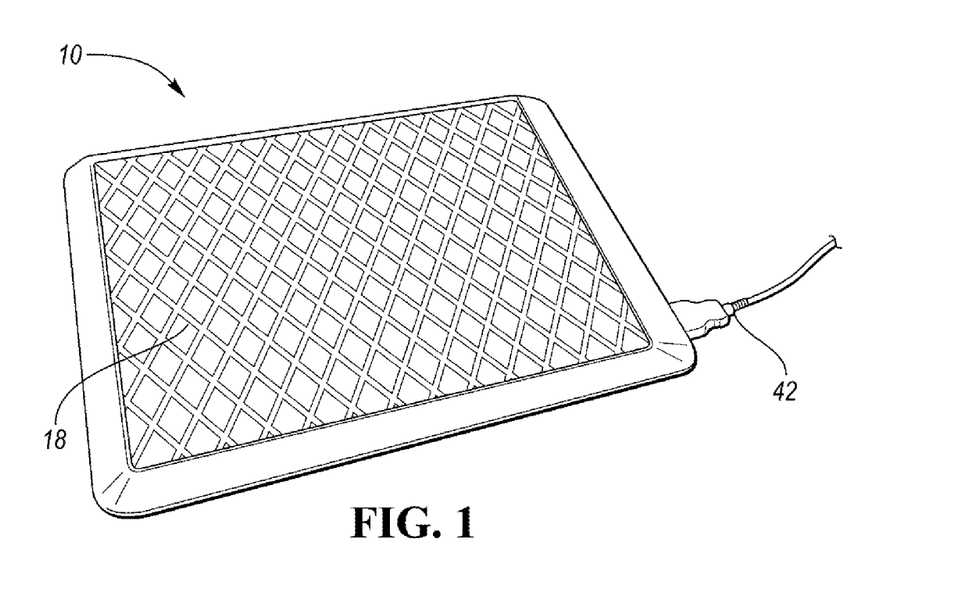
FIG. 1 is a perspective view of a heating pad according to an embodiment.
Figure 2:
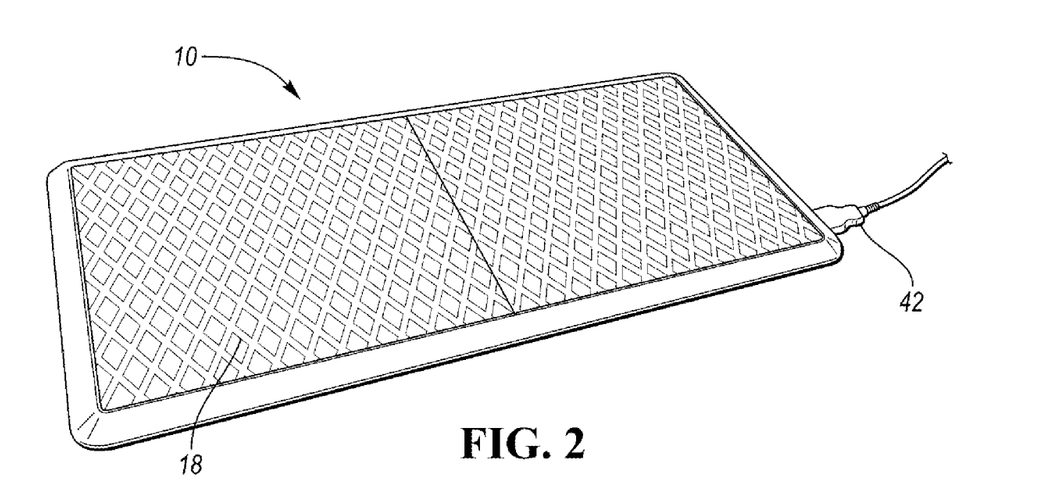
FIG. 2 is a perspective view of a heating pad according to another embodiment.
Figure 3:
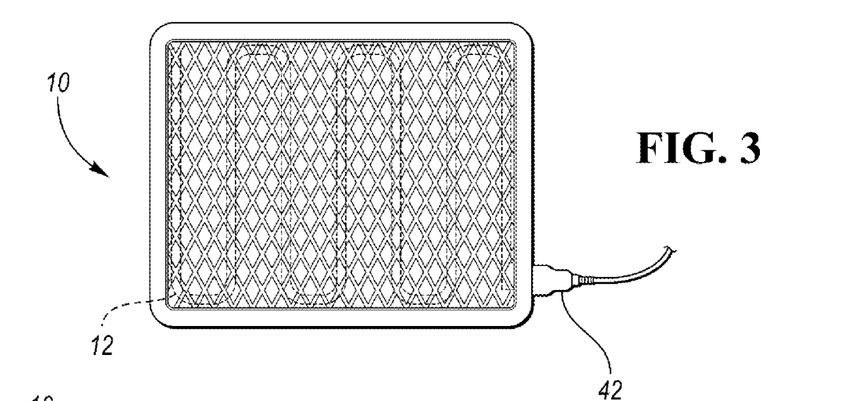
FIG. 3 is a top view of the heating pad of FIG. 1 schematically illustrating the internal heating element.
Figure 4:
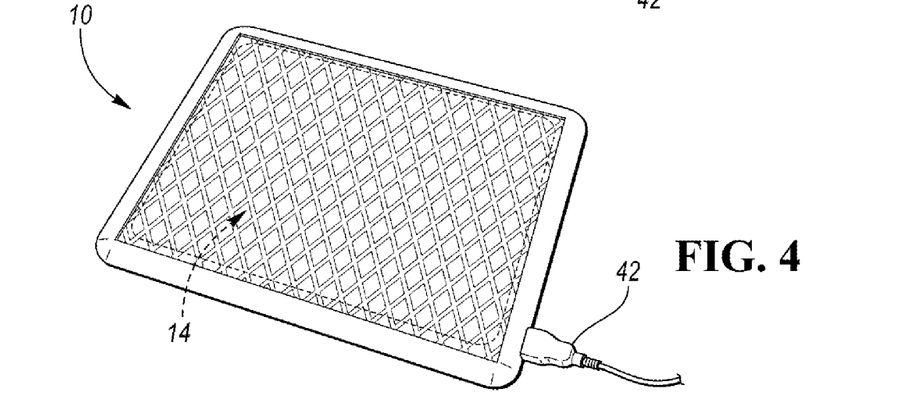
FIG. 4 is a perspective view of the heating pad of FIG. 1 schematically illustrating the internal temperature-retaining component.
Figure 5:
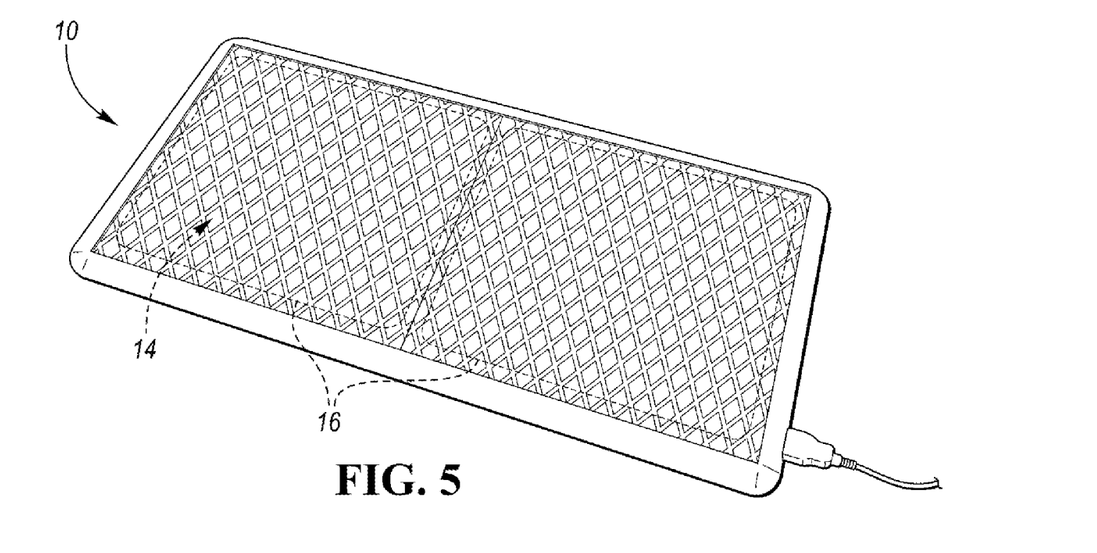
FIG. 5 is a perspective view of the heating pad of FIG. 2 schematically illustrating the internal temperature-retaining component.

FIG. 3 is a top view of the heating pad 10 of FIG. 1 schematically illustrating the internal electric heating element 12. FIGS. 4 and 5 schematically illustrate an internal temperature-retaining component 14 affixed within the heating pad embodiments of FIG. 1 and FIG. 2, respectively, generally adjacent to the heating element 12. The temperature-retaining component 14 functions to efficiently retain heat generated by the heating element 12 for continued use of the heating pad 10 for a period of time if the heating element 12 is no longer powered. This configuration provides heat therapy while allowing portability of the heating apparatus and user mobility. The temperature-retaining component 14 may alternatively function to maintain colder temperatures if the heating pad 10 is chilled for cold therapy use.

As depicted in FIG. 3, the heating element 12 may have a sinusoidal or serpentine configuration. The electric heating element 12 may be formed by a thermally conductive wire coated with any heat resistant substance, such as a heat resistant polymer. In one embodiment, the electric heating element 12 includes a heating wire made of a positive temperature coefficient (PTC) material with negative temperature coefficient (NTC) insulation.

The temperature-retaining component 14 may include any fluid or solid heat-retaining material, which in one or more embodiments includes a gel material or layer. The gel material may also function as a cold-retaining material. The temperature-retaining component 14 allows heat to be more efficiently retained within the heating pad 10 for continued use of the heating pad 10 after power has been disconnected. In one non-limiting embodiment, the thermal storage capability of the temperature-retaining component 14 allows heat to be delivered for two to three hours after the power is disconnected from the heating pad 10. The temperature-retaining component 14 also serves to further facilitate and even out the distribution of heat to the user's body. Still further, the temperature-retaining component 14 provides a cushioning interface for additional comfort to the user of the heating pad 10.

With reference to FIG. 5, depending on the dimensions of the heating apparatus, the temperature-retaining component 14 may be divided into a plurality of separate segments 16. These segments 16 may enhance the flexibility of the temperature-retaining component 14 and facilitate a more uniform distribution of the material (e.g. gel) contained therein within the volume of the heating apparatus, preventing disproportionate pooling in some areas and voids in other areas, especially when under pressure against a user's body.

Figure 6:
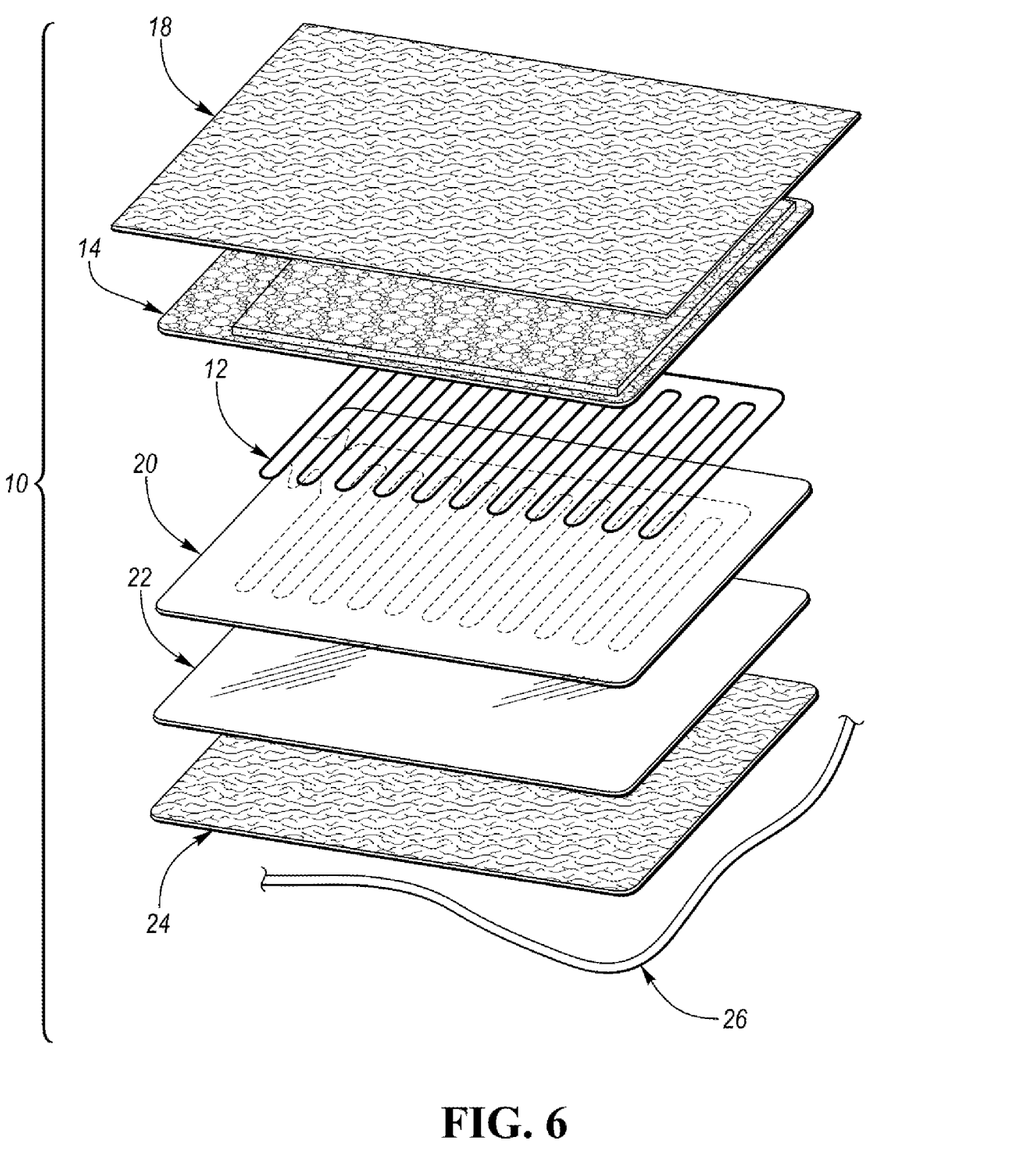
FIG. 6 is an exploded view of a heating pad according to an embodiment.

FIG. 6 is an exploded view of a heating pad 10 according to one or more embodiments. The heating pad 10 has a multi-layered construction and may include a top layer 18 and the temperature-retaining component 14 positioned adjacent to the top layer 18. The electrical heating element 12 may be positioned adjacent to the temperature-retaining component 14, followed by a non-woven scrim material layer 20, a batting material layer 22, and a bottom layer 24. In addition, if desired, a cloth outer covering (not shown) may be provided that encloses the entire heating pad 10.

The top layer 18 and the bottom layer 24 may be constructed of any suitable material such as, but not limited to, polyester. In one embodiment, the top layer 18 and bottom layer 24 are constructed from a micromink material and each may have a thickness of approximately 1 mm, although other thicknesses are also contemplated. The top layer 18 and the bottom layer 24 are secured together, such as along their edges, to form an inner cavity for receiving the various internal layers of the heating pad 10.

In one embodiment, the temperature-retaining component 14 is positioned adjacent an inner surface of the top layer 18. In an alternative embodiment, the temperature-retaining component 14 could form an exterior portion of the heating pad 10, without the top layer 18, such that temperature-retaining component 14 would be in direct contact with the user's body. In one non-limiting example, the temperature-retaining component 14 may be approximately 8 mm thick. The temperature-retaining component 14 may be constructed from spaced sheets of a flexible, liquid-impermeable, plastic material which are secured together to contain the gel material therein. The heating element 12 is substantially uniformly distributed within the heating pad 10 and arranged to effectively and efficiently distribute heat to the temperature-retaining component 14 and the top layer 18 of the heating pad 10.

Padding material is positioned between the electric heating element 12 and the bottom layer 24, and may include a non-woven scrim material layer 20 and a layer of batting material 22 as shown in FIG. 6. The electric heating element 12 may be attached to the scrim material layer 20, where the scrim material layer 20 may be constructed from polyester with a thickness of approximately 0.1 mm, although this dimension is not intended to be limiting. The batting material layer 22 provides a layer of insulation between the electric heating element 12 and the bottom layer 24 of the heating pad 10. The batting material layer 22 may be constructed from any suitable insulative material, such as polyester and, in one non-limiting example, may have a thickness of approximately 1.5 mm. In addition to insulation, the padding material provides additional cushioning and comfort for the user.

The various layers of the heating pad 10 can be manufactured separately and then assembled. After manufacture, the layers of the heating pad 10 are secured together, such as by sewing their edges together. In an alternative embodiment, the top layer 18 and the bottom layer 24 can be constructed from a continuous sheet which may be folded around the internal layers and then secured to assemble the heating pad 10. An edging belt 26 may be sewn or otherwise secured around the edge of the assembled heating pad 10, where the edging belt 26 may be constructed from a polyester material. The multi-layered design of the heating pad 10 provides manufacturing efficiency and flexibility in that the multiple layers of the heating pad 10 can be manufactured at separate times and in separate locations before being assembled into the finished product.

Figure 7:
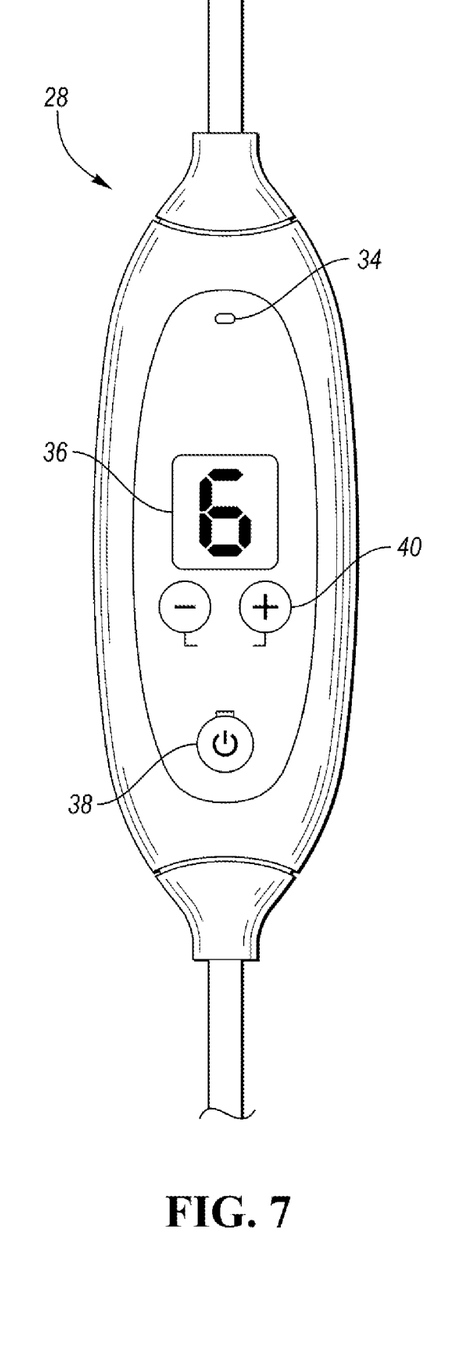
FIG. 7 is a front view of a controller for a heating apparatus according to an embodiment.
Figure 8:
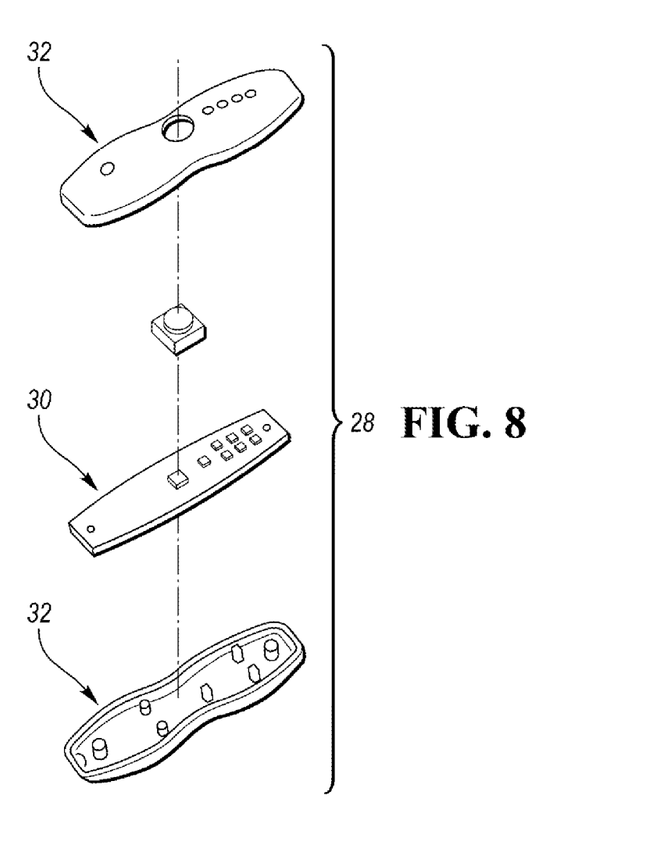
FIG. 8 is an exploded view of a controller and related components for a heating apparatus.

Referring to FIGS. 7 and 8, a controller 28 is in electrical communication with the electric heating element 12. The controller 28 includes a printed circuit board 30 and a housing 32 via which the user may select from various settings to regulate the power supplied to (adjust the temperature of) the electric heating element 12 and thus the temperature of the temperature-retaining component 14 and the heat output of the heating pad 10. In one or more embodiments, the controller 28 includes various user interface features including an LED indicator 34, such as a 2-hour auto-off indicator. The controller 28 also includes a digital display 36 which may indicate the current heat setting, a power button 38, and + and − buttons 40 to toggle the heat setting up and down. The electric heating element 12 and the controller 28 are in electrical communication with a power source, such as a power cord 42 which may receive power from a wall outlet. In one embodiment, the power cord 42 may be detachable from the heating pad 10 to allow for greater portability. The heating pad 10 may, alternatively, include a detachable battery pack (not shown).

The description provided herein for the heating pad 10 embodiment may also be applicable to other heated devices such as, but not limited to, heated blankets, wraps, throws, cushions, and pillows, as described further below.

Figure 9:
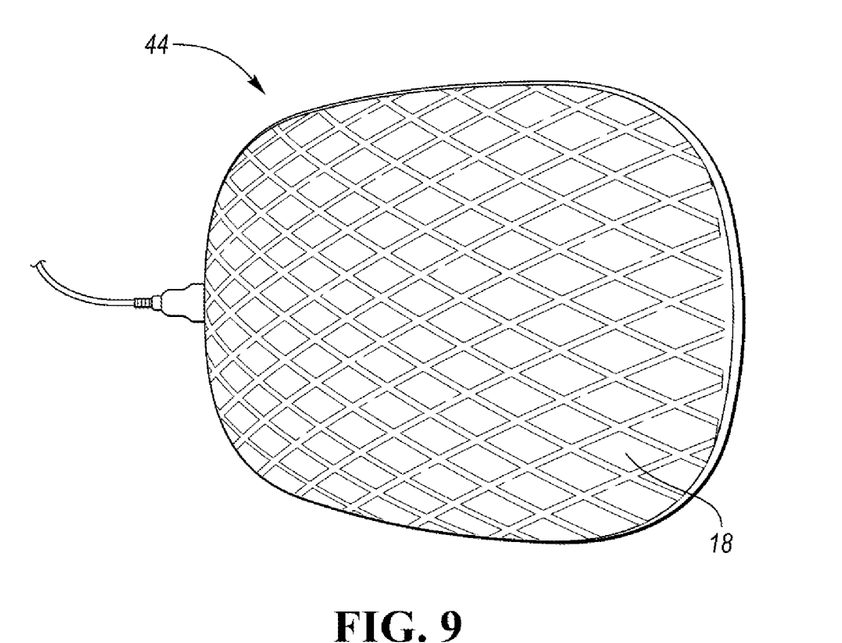
FIG. 9 is a perspective view of a heated pillow according to an embodiment.
Figure 10:
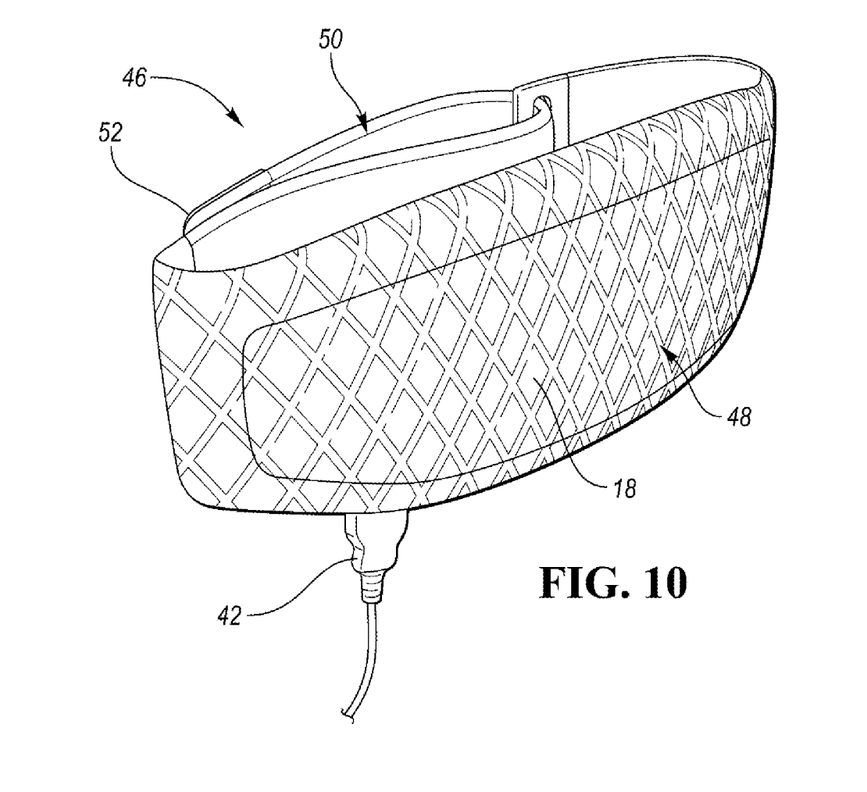
FIG. 10 is a front perspective view of a heated belt wrap according to an embodiment.
Figure 11:
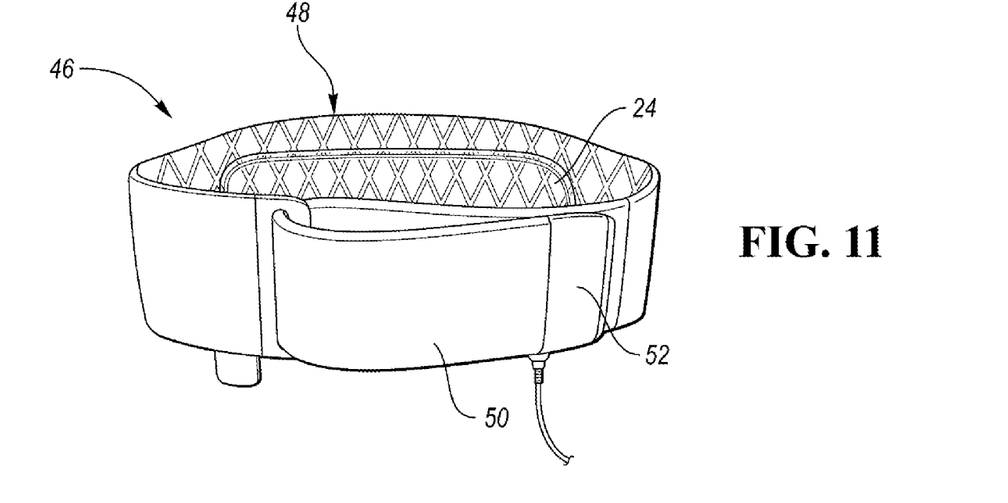
FIG. 11 is a rear perspective view of the heated belt wrap.
Figure 12:
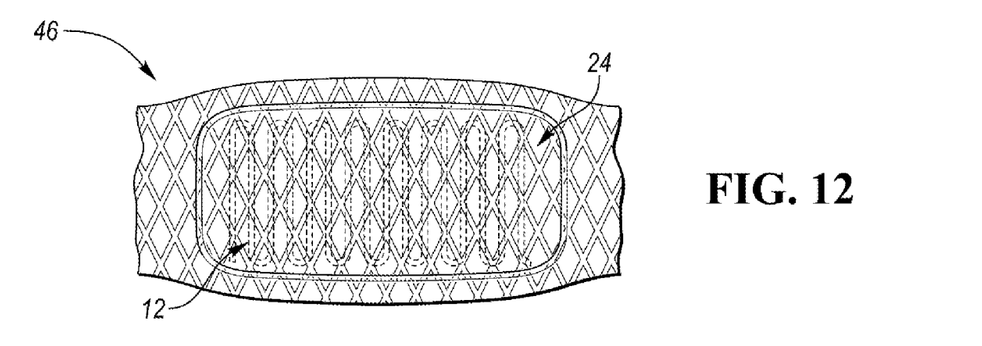
FIG. 12 is a front view of an inner side of the heated belt wrap schematically illustrating the internal heating element.

As a first example, FIG. 9 illustrates a heated pillow 44 according to an embodiment. As shown, the heated pillow 44 may have a relatively smaller, more rounded appearance than the heating pad 10, and may also include an increased thickness of the padding material, if desired. The construction and features of the heating pad 10 may be equally applicable to the heated pillow 44.

Turning to FIGS. 10-13, a heated belt wrap 46 is illustrated. In addition to the construction and features described above for the heating pad 10, the heated belt wrap 46 includes an elongated main body 48 with an adjustable strap 50 extending therefrom. The strap 50 can be adjusted in length to fit the size of the user's desired body treatment area, and in one non-limiting embodiment may be constructed from an elastic material. A releasable closure 52 is disposed on the strap 50 to secure it to the main body 48 at desired position, wherein the releasable closure 52 may comprise a fastener, such as a hook and loop material (e.g. Velcro®).

Figure 13:
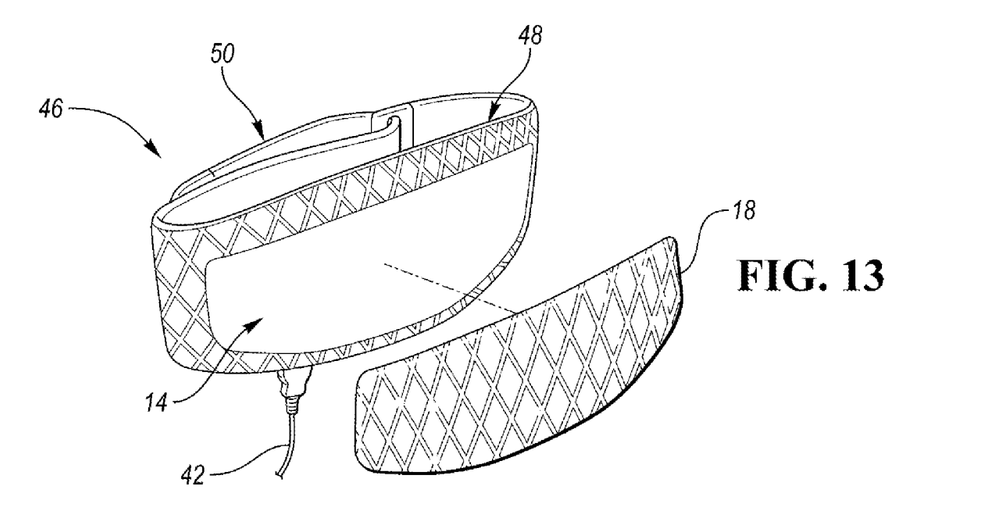
FIG. 13 is a perspective view of the heated belt wrap with an outer side removed to schematically illustrate the internal temperature-retaining component.
Figure 14:
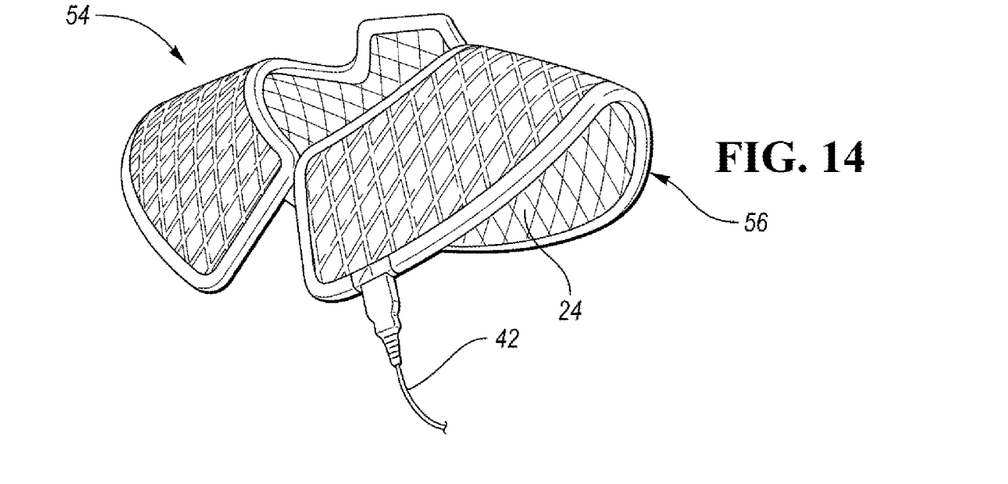
FIG. 14 is a front perspective view of a heated neck and shoulder wrap according to an embodiment.
Figure 15:
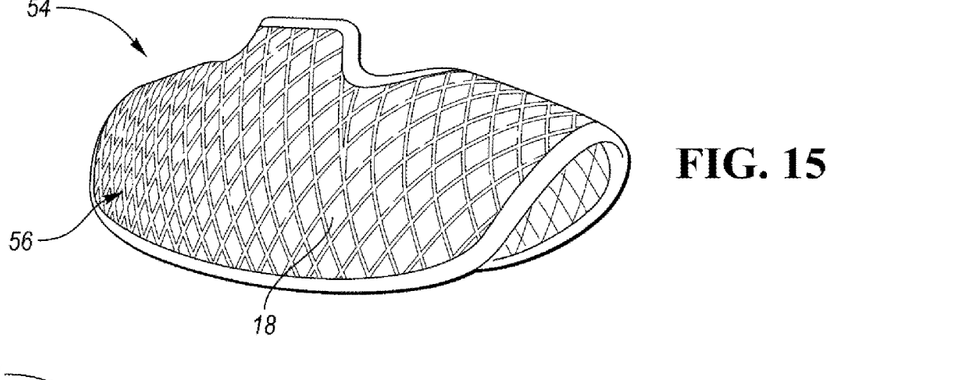
FIG. 15 is a rear perspective view of the heated neck and shoulder wrap.
Figure 16:
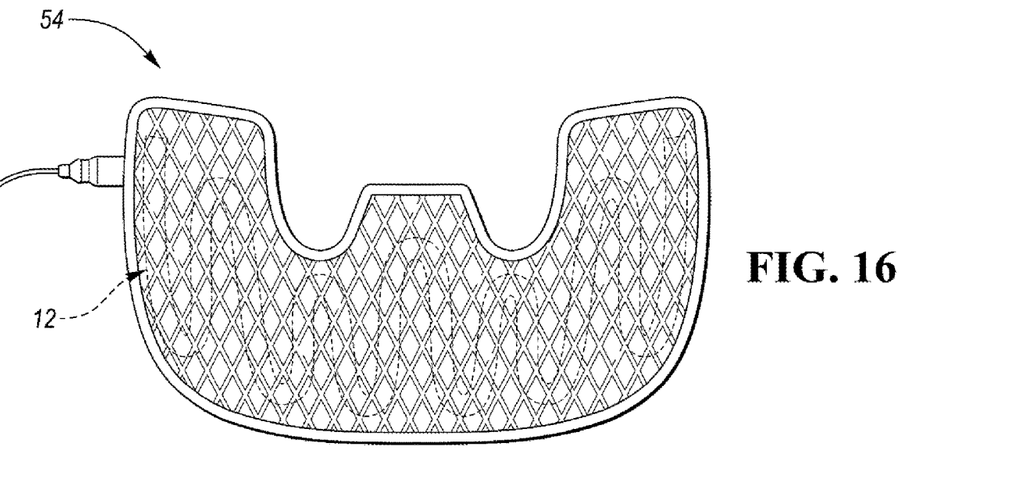
FIG. 16 is a front view of an inner side of the heated neck and shoulder wrap schematically illustrating the internal heating element.
Figure 17:
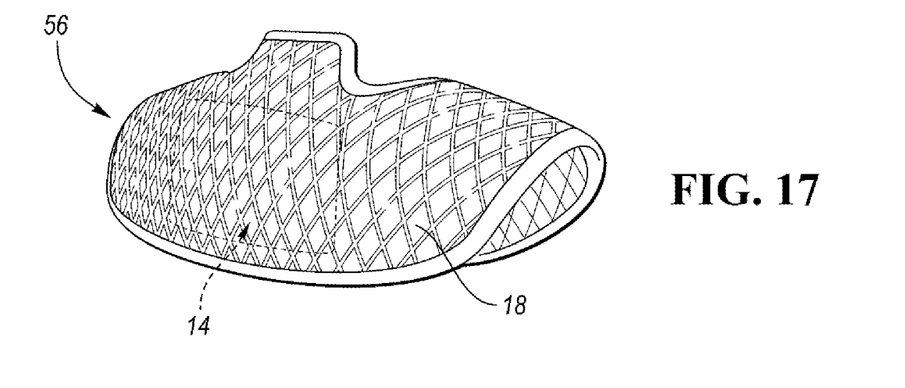
FIG. 17 is a perspective view of the outer side of the heated neck and shoulder wrap schematically illustrating the internal temperature-retaining component.

The heating element 12 and the temperature-retaining component 14 may be sized to substantially fill the area of the main body 48. As with the heating pad 10, the temperature-retaining component 14 may be adjacent the top layer 18. In one embodiment, the heated belt wrap 46 may be reversible, such that the top layer 18 may be placed in contact with the user's body part. This arrangement may be especially beneficial if the temperature-retaining component 14 is chilled and used for cold therapy. As illustrated in FIG. 13, optionally a portion of the top layer could be removable to allow for direct contact of the temperature-retaining component 14 with the user's skin.

Figure 18:
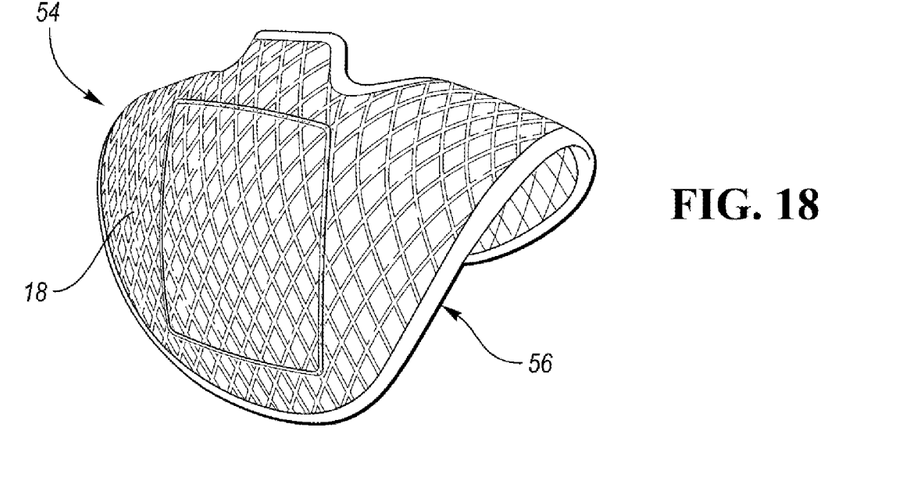
FIG. 18 is a rear perspective view illustrating a heated neck and shoulder wrap according to another embodiment.
Figure 19:
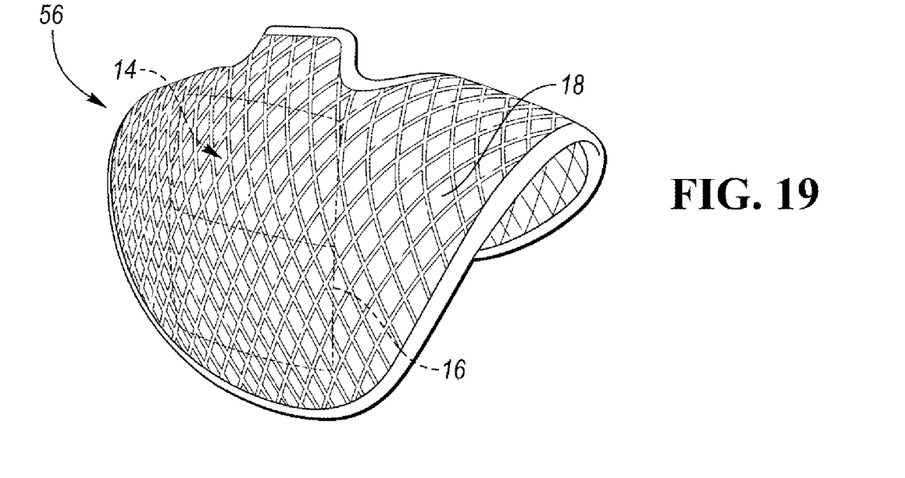
FIG. 19 is a rear perspective view of the outer side of the heated neck and shoulder wrap of FIG. 18 schematically illustrating the internal temperature-retaining component.
Figure 20:
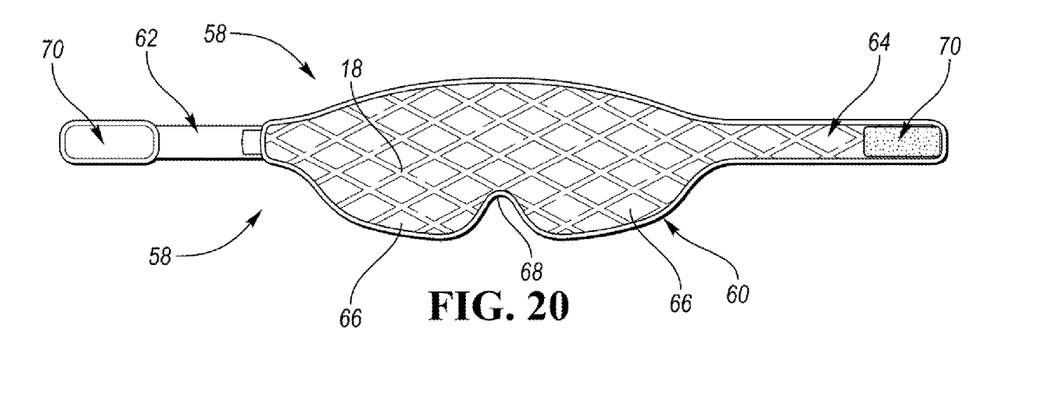
FIG. 20 is a front view of an outer side of a heated eye wrap according to an embodiment.
Figure 21:
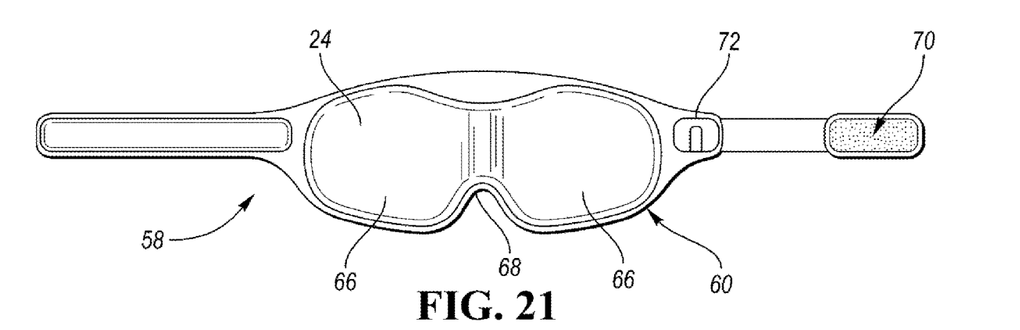
FIG. 21 is a front view of an inner side of the heated eye wrap of FIG. 20.

FIGS. 14-17 illustrate a first embodiment of a heated neck and shoulder wrap 54 having a back portion 56. FIGS. 18 and 19 show a heated neck and shoulder wrap 54 according to another embodiment, wherein a larger back portion 56 is utilized and contains a temperature-retaining component 14 with a plurality of segments 16. In one non-limiting embodiment, the heating element 12 may span substantially an entire area of the neck and shoulder wrap 54, whereas the temperature-retaining component 14 may be disposed only in the back portion 56. In one embodiment, the heated neck and shoulder wrap 54 may be reversible, such that the top layer 18 may be placed in contact with the user's body part. This arrangement may be especially beneficial if the temperature-retaining component 14 is chilled and used for cold therapy. Again, the construction and features of the heating pad 10 may be equally applicable to the heated neck and shoulder wrap 54.

Turning to FIGS. 20-25, a heated eye wrap 58 is illustrated according to an embodiment. In addition to the construction and features described above for the heating pad 10, the heated eye wrap 58 includes a main body 60 with a first strap 62 and a second strap 64 extending therefrom. The main body 60 may have an elongated configuration which generally resembles goggles, with two eye portions 66 sized to cover each of a user's eyes and an indentation 68 therebetween sized to accommodate a user's nose. According to one embodiment, at least one of the first strap 62 and the second strap 64 may be constructed from an elastic material (i.e. shown as the first strap 62 in FIGS. 20-22) to provide universal adjustability around a user's head. The first and second straps 62, 64 each have a releasable closure 70 which may comprise a fastener, such as a hook and loop material (e.g. Velcro®). When secured to the user's head, the first and second straps 62, 64 may be sized to be disposed above the top of a user's ears, preventing uncomfortable chafing and muffling of sound.

Figure 22:
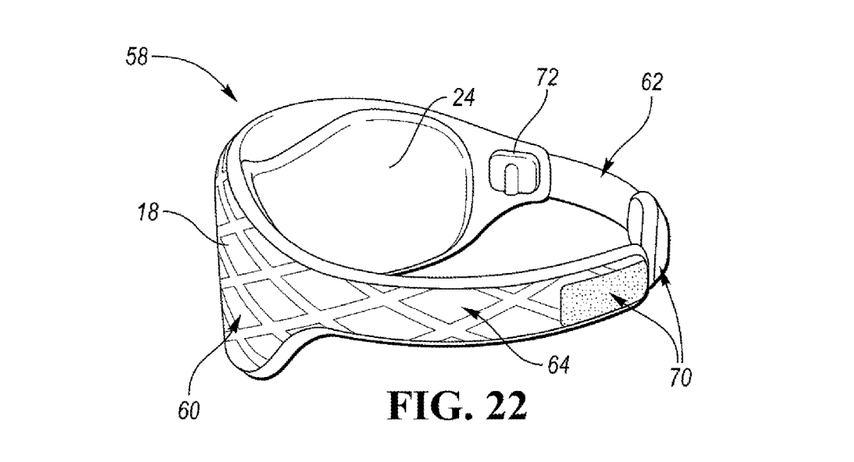
FIG. 22 is a rear perspective view of the heated eye wrap.
Figure 23:
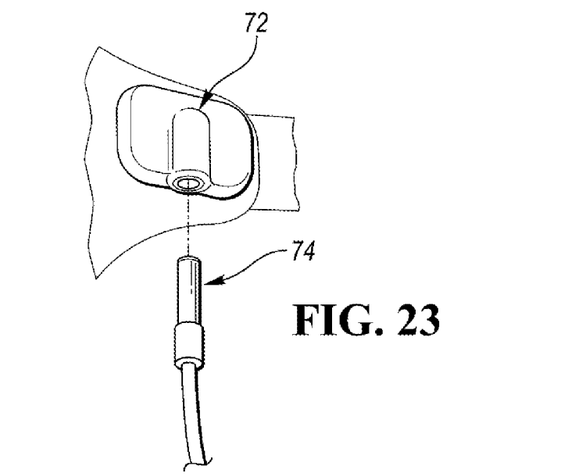
FIG. 23 is a cut away view of the connector of the heated eye wrap.
Figure 27:
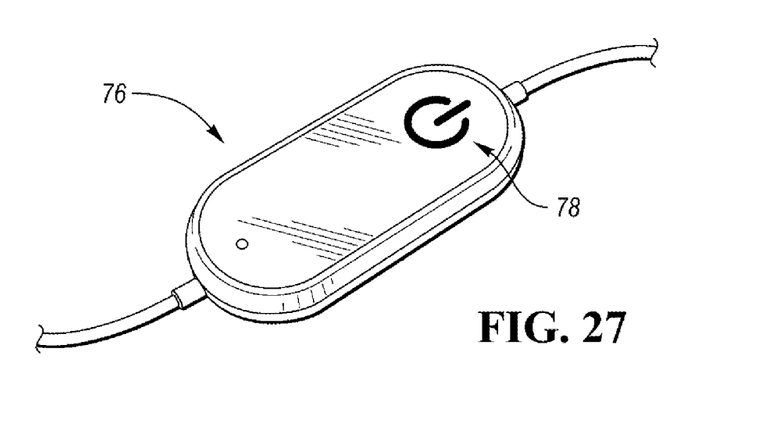
FIG. 27 is a controller for the heated eye wrap according to an embodiment.

As shown in FIGS. 22 and 23, a power adapter port 72 may be provided on the bottom layer 24 of the main body 60, and may be covered with fabric (e.g. micromink) for comfort. The port 72 may be configured to removably receive a connector 74 for a power line or a controller 76, such as shown in FIG. 27. The controller 76 may include a translucent power icon 78 which indicates the heat level, and an audible indicator that emits different tones depending on heat level, allowing for blindfolded use.

Figure 24:
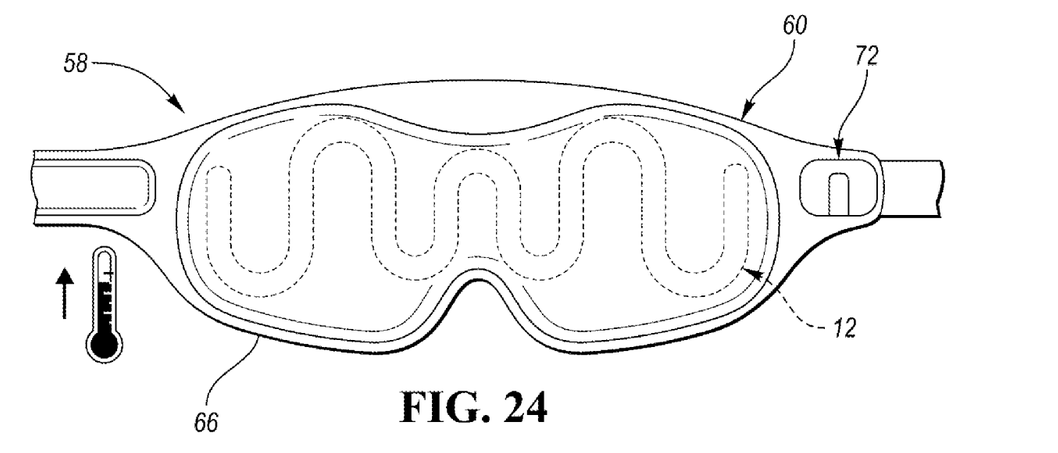
FIG. 24 is a rear view of the heated eye wrap schematically illustrating the internal heating element.
Figure 25:
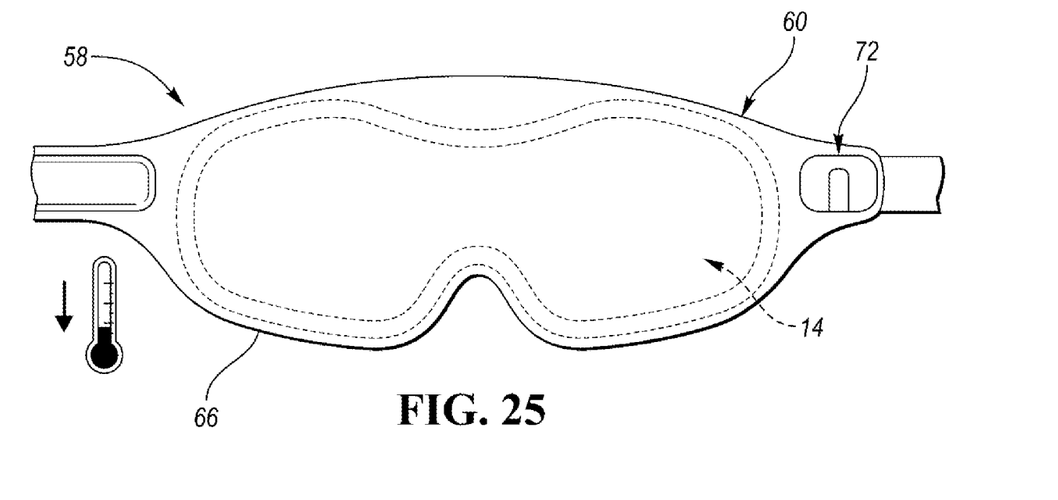
FIG. 25 is a rear view of the heated eye wrap illustrating the internal temperature-retaining component.
Figure 26:
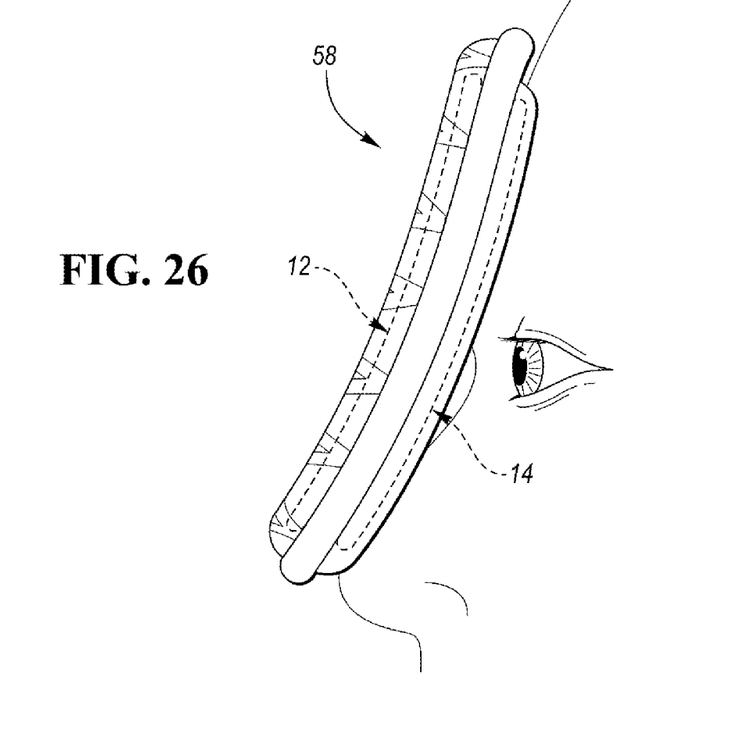
FIG. 26 is a schematic, cross-sectional illustration of the internal heating element and the internal temperature-retaining component in the heated eye wrap and its positioning with respect to a user's face.

As shown in FIGS. 24 and 25, the heating element 12 and the temperature-retaining component 14 may be sized to substantially fill the area of the main body 60. Although not shown, it is understood that the temperature-retaining component 14 could be configured with a plurality of segments 16, such as one segment 16 in each eye portion 66 of the main body 60. With reference to FIG. 26, the heated eye wrap 58 may have a configuration where the temperature-retaining component 14 is adjacent the inner or bottom layer 24, closer to the user's eyes and face compared with the heating element 12. In operation, the heating element 12 heats up the temperature-retaining component 14, providing uniform, diffused soothing heat to the eye region of the user which can be retained for extended periods of time. When the eye wrap 58 is chilled prior to use, the temperature-retaining component functions to cool the bottom layer 24 against the user's skin. Alternatively, the temperature-retaining component 14 may be adjacent the outer or top layer 18, and the eye wrap 58 could also be reversible.

While exemplary embodiments are described above, it is not intended that these embodiments describe all possible forms of the invention. Rather, the words used in the specification are words of description rather than limitation, and it is understood that various changes may be made without departing from the spirit and scope of the invention.

Additionally, the features of various implementing embodiments may be combined to form further embodiments of the invention.

What is claimed is:

1. A portable heating apparatus, comprising:
   a top layer;
   a bottom layer connected to the top layer to form a cavity;
   an electric heating element disposed within the cavity;
   a temperature-retaining layer disposed within the cavity adjacent to the electric heating element and adjacent to the top layer and including a temperature-retaining gel therein, wherein the temperature-retaining layer is divided into a plurality of separate segments which prevent flow of the temperature-retaining gel between the plurality of separate segments; and
   a power cord in electrical communication with the electric heating element and connectable to a power source to provide power to the electric heating element, the power cord detachable from the portable heating apparatus;
   wherein the temperature-retaining layer retains heat generated by the electric heating element and creates a generally uniform distribution of heat across the top layer.

2. The portable heating apparatus of claim 1, wherein the electric heating element includes a heating wire constructed from a positive temperature coefficient (PTC) material with negative temperature coefficient (NTC) insulation.

3. The portable heating apparatus of claim 1, further comprising a padding material disposed within the cavity between the electric heating element and the bottom layer.

4. The portable heating apparatus of claim 3, wherein the padding material includes a non-woven scrim material layer and a batting material layer.

5. The portable heating apparatus of claim 1, wherein the top layer and the bottom layer are constructed from a micromink material.

6. The portable heating apparatus of claim 1, wherein a portion of the top layer is removable to expose the temperature-retaining layer to an exterior of the portable heating apparatus.

7. The portable heating apparatus of claim 1, further comprising a controller in electrical communication with the electric heating element for regulating power to the electric heating element.

8. The portable heating apparatus of claim 7, wherein the controller includes an audible indicator that emits different tones depending on a heat level of the electric heating element.

9. A portable heating apparatus, comprising:
   a top layer;
   a bottom layer connected to the top layer to form a cavity;
   an electric heating element disposed within the cavity;
   a padding material disposed within the cavity between the electric heating element and the bottom layer;
   a gel layer affixed within the cavity between the electric heating element and the top layer and including a temperature-retaining gel therein, wherein the gel layer is divided into a plurality of separate segments which prevent flow of the temperature-retaining gel between the plurality of separate segments; and
   a power cord in electrical communication with the electric heating element and connectable to a power source to provide power to the electric heating element, the power cord detachable from the portable heating apparatus;
   wherein the gel layer retains heat generated by the electric heating element and creates a generally uniform distribution of heat across the top layer, and the gel layer maintains a cold temperature generated by chilling the portable heating apparatus.

10. The portable heating apparatus of claim 9, wherein a portion of the top layer is removable to expose the gel layer to an exterior of the portable heating apparatus.

11. A portable heating apparatus, comprising:
    a main body including an outer, top layer and an inner, bottom layer connected to the top layer, the top and bottom layers forming a cavity therebetween;
    a first strap and a second strap extending from the main body;
    an electric heating element disposed within the cavity;
    a temperature-retaining layer disposed within the cavity adjacent to the electric heating element and adjacent to the bottom layer and including a temperature-retaining gel therein, wherein the temperature-retaining layer is divided into a plurality of separate segments which prevent flow of the temperature-retaining gel between the plurality of separate segments; and
    a power cord in electrical communication with the electric heating element and connectable to a power source to provide power to the electric heating element, the power cord detachable from the portable heating apparatus;
    wherein the temperature-retaining layer retains heat generated by the electric heating element and creates a generally uniform distribution of heat across the bottom layer.

12. The portable heating apparatus of claim 11, wherein the main body has an elongated configuration with two eye portions each sized to cover an eye of a user and an indentation therebetween sized to accommodate a nose of the user.

13. The portable heating apparatus of claim 11, wherein at least one of the first strap and the second strap is constructed from an elastic material, and wherein the first and second straps each have a releasable closure.

14. The portable heating apparatus of claim 11, further comprising a power adapter port provided on the bottom layer of the main body.

15. The portable heating apparatus of claim 11, further comprising a controller in electrical communication with the electric heating element for regulating power to the electric heating element, wherein the controller includes an audible indicator that emits different tones depending on a heat level of the electric heating element.

* * * * *